US007227012B1

(12) United States Patent
Markham et al.

(10) Patent No.: US 7,227,012 B1
(45) Date of Patent: Jun. 5, 2007

(54) **LATENCY-ASSOCIATED REGULATORY REGION FROM *HERPESVIRUS SAIMIRI* (HVS)**

(75) Inventors: Alexander Fred Markham, Leeds (GB); Adrian Whitehouse, Leeds (GB); Kersten Hall, Leeds (GB); David Meredith, deceased, late of Leeds (GB); by Aida Meredith, legal representative, Leeds (GB)

(73) Assignee: The University of Leeds (GB)

( * ) Notice: Subject to any disclaimer, the term of this patent is extended or adjusted under 35 U.S.C. 154(b) by 0 days.

(21) Appl. No.: 09/913,970

(22) PCT Filed: Feb. 18, 2000

(86) PCT No.: PCT/GB00/00537

§ 371 (c)(1),
(2), (4) Date: Mar. 28, 2002

(87) PCT Pub. No.: WO00/49167

PCT Pub. Date: Aug. 24, 2000

(30) Foreign Application Priority Data

Feb. 19, 1999 (GB) ................................ 9903694.9

(51) Int. Cl.
*C07H 21/04* (2006.01)
*A61K 48/00* (2006.01)

(52) U.S. Cl. ....................... 536/24.1; 536/23.1; 514/44

(58) Field of Classification Search ............... 536/24.1; 514/44

See application file for complete search history.

(56) References Cited

FOREIGN PATENT DOCUMENTS

| | | |
|---|---|---|
| EP | 0362732 A | 4/1990 |
| WO | WO9810083 A | 3/1998 |

OTHER PUBLICATIONS

Arnone et al. The hardwiring of development: organization and function of genomic regulatory systems. Development. May 1997;124(10):1851-64.*

Nicholas et al. Analysis of nucleotide sequence of the rightmost 43 kbp of *Herpevirus saimiri* (HVS) L-DNA: general conservation of genetic organization between HVS and Epstein-Barr virus. Virology. May 1992;188(1):296-310.* pUC18, pUC19: description & restriction map, available at www.fermentas.com/techinfo/nucleic acids/mappuc1819.htm.*

International Search Report for PCT/GB00/00537, dated May 26, 2000.

J. Nicholas et al. "*Herpesvirus saimiri* encodes homologues of G-protein-coupled receptors and cyclins," *Nature* 355, 362-365 (1992).

* cited by examiner

*Primary Examiner*—Daniel M. Sullivan
(74) *Attorney, Agent, or Firm*—Myers Bigel Sibley & Sajovec, P.A.

(57) ABSTRACT

A nucleic acid encoding a promoter and comprising a nucleic acid sequence of SEQ ID NO:1, fragments and/or variants thereof, for use in gene therapy derived from the *Herpesvirus saimiri* (HVS) ORF73 (ECLFI) gene. The invention also includes a gene therapy system and an HVS vector system including the promoter.

5 Claims, 7 Drawing Sheets

Latency-associated regulatory region
(Initiation codon of ORF 73 shown in bold)

FIGURE 1 : SEQ ID NO: 1

```
5' ACCCAGAGAGCTGGACACTAGAACTAGAACCTAATGCATCAAAGCATTATGAATC
TTTATGGCTCAACTTTCACGTTCCTCAAACTACTAAAAGCATTATATTACAAGCCCT
TCGTGGCACAATTTTCCAGGATGGCTTGTGGCAAGTACTTGGACTGAGATACAAACA
CGATGCTCAAGAATATATTATGCAACAAAATGGAACAATTGCAATGAGTTATCATAG
TGCTAAGATAAATCCTTACTTGTATGCAATGCATTATCCAAGGAACCCCTCTGGCAA
TTCATCTGTAGCTGGCATATGTTCAAAGAATGGCAGGCATCTTGCGTTGCTTGTAGA
ACCAGCCCTTTCTTTTCATACTTGGCAATGGCAACATATACCTAAACCTCTAGTAAC
TTCTCCATGGGCATTAATGTATCAATGTATGTTCTTGTGGTGTGTAAAAGAATGATT
GTACTAAGGAACAGTAATAAAAACTCTGACACTAAGATACGATAATATAACTATTTA
TTTATCAAGTGAGCCGCTCTACACTCTAACAGTGACAAATAGTTTTACACCATGCAG
CCATGCGCTGCCTAAAGAGACTTCCAAACATAGCAAACATCAGAGGTAACATACAAT
AATATAGTACCAACAGCATATATGTACATTGAATTCCATACACTATAGCAGATCTCT
TTGCACATGTCTCTTCTATTACACCAACACGCAACAAAGTATCAATGCTTTCCATAA
TATAGTATGGTATACAAAACACTATGAATAGCAGTGTTGTCATTGTAATTATCGTGA
CTACCTCTGCTCTTTTAGACAGCTTTGTCTTGAATAACTTATAACATGACATACTAT
AGCATATTACAGTAATAAAGAGGGGTCCTGCAAAGCTATACCATGTGTGAAAAGTGT
TTAGCTTTGTGCGTAGCTGCTCAGTCAACACACCATCCTCCTCTATGCAAGAAGATG
GTTCATAATATGATGTCACCATCACATGAGGAAGTGCTCCAAAGCAGGCTAATACAA
ATGAACAGCACAGAAATACTTGCCCAATAAGAGTCTTTTTCACCCACAGTCTAGTAG
CACAAAATATTAGCAGACAACGCAAGACACTAATAAAAACTAATATGAAAGGAGACC
AATAAATGCTGAGATTTAAGAAAAAAGCTTCCAGCTTACACAGCTCAGTATTCATAA
AAATTTCAAACATGCGCAAAAGTCTCATTAGCAGATACCCAGCTAAGAACAAGCTGT
TGAGACAAAATCCCATCATCAAGTAGTCAAAACTTTGAGCTTGAGCTCTATACTTTA
GAAAAGTCCTCAGTACAAGAGAATTCCCAATTGCATTGCATAAAAACATCAACACAT
ATATGAATGCTAGTGCACTCTCTGAAATTAAAAAGTTCACTACACACGGCGCTACAT
CTCCATAATATATGTCTCCACTATAATTGTAAGAATAGTTGCTAAAGTCTTCACTAC
TGAAGTCCAGCTTGACCTCCATAGCGAACTACAAAATAAATTTATATAAATTATTCA
CCCAATAACTTGAAATTTAAAGAATTAGGACAAAAGAATGTATATCCTACCTTTCTT
TGCAGCCTGACAGCAAGCTACTGAAAAGTTACTTTTTATTTTGTTTAGTAGCTAG
GTGTGGTTTTACATATGTTTTGTGGCTACACAGTAGATTTAACAAATAGCCACGCCC
CCTACGCTACGTCTAAGGAGGAGCTTAATTCCAAACGAGTGGCGGGATTTCGCTAAA
GTCACTGAAGAACTTGCATCTTAATTCATCCGCGGCTGCAACCTTCAAACAAAAAAG
GAGGTTTCGATTTTCGATGTGAGTAGCACTTTTACATTTTTACAGTCATAATGTGAC
CAACTTGTAAAAAATGTTATGTTTTATGCCTATATTAGCCACCTAGTGGCTGCTCAT
TGCATAGCTTTTTCAGTTAACGTATAGCGCCATCTAGTGTATAACGTGTTTGTTGCA
ATTATAGATG 3'
```

Figure 4
(a)
EcoD
(b)
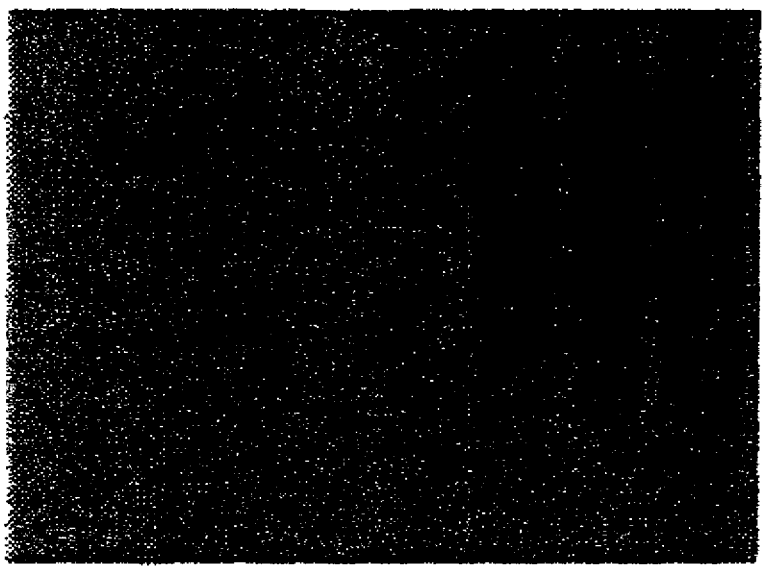
EcoJ
Actin

Figure 5
(a)
EcoC
(b)
KpnE
Actin

Figure 6
(a) ORF71
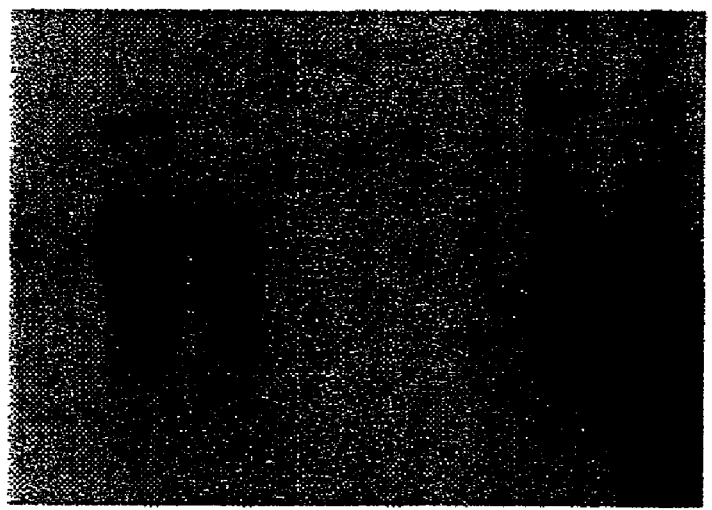
(b) ORF72
(c) ORF73
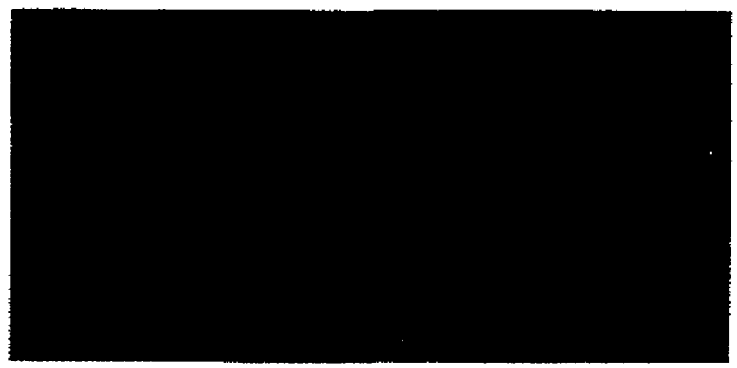
Actin

SEQUENCE LISTING

<160> NUMBER OF SEQ ID NOS: 13

<210> SEQ ID NO 1
<211> LENGTH: 2003
<212> TYPE: DNA
<213> ORGANISM: Homo sapiens

<400> SEQUENCE: 1

```
acccagagag ctggacacta gaactagaac ctaatgcatc aaagcattat gaatctttat      60
ggctcaactt tcacgttcct caaactacta aaagcattat attacaagcc cttcgtggca     120
caattttcca ggatggcttg tggcaagtac ttggactgag atacaaacac gatgctcaag     180
aatatattat gcaacaaaat ggaacaattg caatgagtta tcatagtgct aagataaatc     240
cttacttgta tgcaatgcat tatccaagga acccctctgg caattcatct gtagctggca     300
tatgttcaaa gaatggcagg catcttgcgt tgcttgtaga accagccctt tcttttcata     360
cttggcaatg gcaacatata cctaaacctc tagtaacttc tccatgggca ttaatgtatc     420
aatgtatgtt cttgtggtgt gtaaaagaat gattgtacta aggaacagta ataaaaactc     480
tgacactaag atacgataat ataactattt atttatcaag tgagccgctc tacactctaa     540
cagtgacaaa tagttttaca ccatgcagcc atgcgctgcc taaagagact tccaaacata     600
gcaaacatca gaggtaacat acaataatat agtaccaaca gcatatatgt acattgaatt     660
ccatacacta tagcagatct ctttgcacat gtctcttcta ttacaccaac acgcaacaaa     720
gtatcaatgc tttccataat atagtatggt atacaaaaca ctatgaatag cagtgttgtc     780
```

-continued

```
attgtaatta tcgtgactac ctctgctctt ttagacagct ttgtcttgaa taacttataa      840
catgacatac tatagcatat tacagtaata aagaggggtc ctgcaaagct ataccatgtg      900
tgaaaagtgt ttagctttgt gcgtagctgc tcagtcaaca caccatcctc ctctatgcaa      960
gaagatggtt cataatatga tgtcaccatc acatgaggaa gtgctccaaa gcaggctaat     1020
acaaatgaac agcacagaaa tacttgccca ataagagtct ttttcaccca cagtctagta     1080
gcacaaaata ttagcagaca acgcaagaca ctaataaaaa ctaatatgaa aggagaccaa     1140
taaatgctga gatttaagaa aaaagcttcc agcttacaca gctcagtatt cataaaaatt     1200
tcaaacatgc gcaaaagtct cattagcaga tacccagcta agaacaagct gttgagacaa     1260
aatcccatca tcaagtagtc aaactttga gcttgagctc tatactttag aaaagtcctc      1320
agtacaagag aattcccaat tgcattgcat aaaaacatca acacatatat gaatgctagt     1380
gcactctctg aaattaaaaa gttcactaca cacggcgcta catctccata atatatgtct     1440
ccactataat tgtaagaata gttgctaaag tcttcactac tgaagtccag cttgacctcc     1500
atagcgaact acaaaataaa tttatataaa ttattcaccc aataacttga aatttaaaga     1560
attaggacaa aagaatgtat atcctacctt tctttgcagc ctgacagcaa gctactgaaa     1620
aagttacttt ttattttgtt ttagtagcta ggtgtggttt tacatatgtt ttgtggctac     1680
acagtagatt taacaaatag ccacgccccc tacgctacgt ctaaggagga gcttaattcc     1740
aaacgagtgg cgggatttcg ctaaagtcac tgaagaactt gcatcttaat tcatccgcgg     1800
ctgcaacctt caaacaaaaa aggaggtttc gattttcgat gtgagtagca cttttacatt     1860
tttacagtca taatgtgacc aacttgtaaa aaatgttatg ttttatgcct atattagcca     1920
cctagtggct gctcattgca tagcttttc agttaacgta tagcgccatc tagtgtataa     1980
cgtgtttgtt gcaattatag atg                                             2003
```

<210> SEQ ID NO 2
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 2

```
cgcggatccg gcaaggtcac ttcgccctat ctg                                    33
```

<210> SEQ ID NO 3
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 3

```
ccggaattcc tgtgttacac ataacagact                                        30
```

<210> SEQ ID NO 4
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 4

```
cgcggatccg ctgcaatggc agattcacc                                         29
```

<210> SEQ ID NO 5
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 5
ccggaattcg gtctgcagtt agtgttgtca g          31

<210> SEQ ID NO 6
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 6
acgcgtcgac ccatctataa ttgcaacaaa cacc       34

<210> SEQ ID NO 7
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 7
cccaagcttc acatatatga atgctagtgc ac         32

<210> SEQ ID NO 8
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 8
acgcgtcgac ccatctataa ttgcaacaaa cacg       34

<210> SEQ ID NO 9
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 9
cccaagaata acatatatga atgctagtgc ac         32

<210> SEQ ID NO 10
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 10
gcactgcagc accatcacat gaggaggtgc            30

<210> SEQ ID NO 11
<211> LENGTH: 32
<212> TYPE: DNA
<213> ORGANISM: Artificial sequence
<220> FEATURE:
<223> OTHER INFORMATION: Synthetic oligonucleotide -continued

```
<400> SEQUENCE: 11
gcactgcagc catgcagcag ccatgcgctg cc                                    32

<210> SEQ ID NO 12
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 12
gcactgcagc ccagagagct ggacactag                                        29

<210> SEQ ID NO 13
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 13
cgcggatccc catctataat tgcaacaaac acg                                   33
```

LATENCY-ASSOCIATED REGULATORY REGION FROM *HERPESVIRUS SAIMIRI* (HVS)

RELATED APPLICATION INFORMATION

This application claims priority under 35 U.S.C. § 371 from PCT Application No. PCT/GB00/00537 (published under PCT Article 21(2) in English), filed on Feb. 18, 2000, which claims the benefit of Great Britain Application Serial No. 9903694.9, filed on Feb. 19, 1999, the disclosures of which are incorporated by reference herein in their entireties.

The present invention relates to a method of virus manipulation; means therefor and products thereof which have particular, but not exclusive, application in gene therapy/vaccine development.

BACKGROUND TO THE INVENTION

*Herpesvirus saimiri* (HVS) is a lymphotropic rhadinovirus (γ-2 herpesvirus) which causes persistent infection in its natural host the squirrel monkey (*Saimiri sciureus*) without causing any obvious symptoms of disease. HVS has been subdivided into three groups (A, B and C) on the basis of the sequence of the open reading frame of *H. saimiri* transformation-associated protein (STP) (Fleckenstein & Desrosiers, 1982; Medveczky et al., 1984). The structure of the HVS genome consists of a unique, low G+C content DNA segment (L-DNA) approximately 110 kb in length, flanked by multiple tandem repeats of high G+C content DNA (H-DNA) (Albrecht et al., 1992; Bankier et al., 1985). Analysis indicates it shares limited homology with other herpesviruses. Examples of such herpesviruses include Epstein Barr Virus (EBV), bovine herpesvirus 4 and murine gammaherpesvirus 68 (MHV68) (Blubot et al., 1992; 1996; Virgin et al., 1997). The genomes of EBV, BHV, MHV68 and HVS have been shown to be generally co-linear, in that homologous sequences are found in approximately equivalent locations and in the same relative orientation. However, conserved gene blocks are separated by unique genes with respect to each virus (Virgin et al., 1997). Genes which are expressed in HVS in the latent state are currently unknown.

HVS has a number of features which make it an attractive candidate for use as a gene delivery vector. These include the potential to package and deliver in excess of 50 kb of heterologous DNA, the ability to infect non-dividing cells and the maintenance of the viral genome as a stable episome in a latently infected host cell. The ability of herpes viruses to adopt a latent state in infected cells is a particularly attractive feature in terms of their use as gene delivery vehicles. In addition, because HVS is a non-human pathogen, it should not elicit a primary immune response on introduction into a human host. Primary immune response is a fundamental problem associated with human herpesvirus gene delivery systems which reduces the efficency of these vectors.

In our studies, we generated a recombinant HVS based on the non-transforming strain A11, which expresses the green fluorescent protein (GFP) gene (Whitehouse et al., 1998b). This virus contains the GFP gene under the control of the constitutive human cytomegalovirus (HCMV) early promoter inserted into the rightmost flanking region of H-DNA. We have demonstrated that this recombinant HVS-GFP was able to infect a wide range of human cancer cell lines, including T-cell (Jurkat), pancreatic (MIAPACA), colorectal (SW480) and lung carcinoma cells (A549). Thus, we have continued investigation of this recombinant HVS as we believe it to be an ideal candidate as a gene delivery vector.

The use of an efficient promoter which can drive stable long term expression of a transgene is a prerequisite for the development of any gene delivery vector. A variety of promoters have been utilised in herpes simplex virus (HSV) vectors including neuronal-specific promoters such as the neurone-specific enolase promoter, the neurofilament promoter and tyrosine hydroxylase promoter, as well as viral promoters such as the HSV thymidine kinase promoter and the HCMV immediate early promoter. Studies showed, however, that these promoters are unsuitable for long term expression in vivo, due to promoter silencing effects (Fink et al., 1996; Glorioso et al., 1992; 1995). There is a need, therefore, to identify viral regulatory regions which can be used to drive stable long term expression of a transgene.

Recently, recombinant HSV-1 viruses have been produced in which expression of the lacZ and lacZ-neo cassettes are driven by the latency-associated-transcript (LAT) promoter (Lachmann & Efstathiou, 1997). Peripheral infection of neurones with these viruses results in stable long-term expression of a β-galactosidase transgene for at least 190 days post-infection. Therefore, we believe that it would be advantageous to identify and characterise HVS regulatory regions associated with latency, if they exist, to drive long term stable expression of heterologous transgenes for the future development of HVS as a gene delivery system. In the course of our investigations to identify viral regulatory regions which can be used to drive stable long term expression of a transgene, we serendipitously identified a cluster of HVS genes which are apparently expressed specifically in the latent state and we provide evidence to this effect. The DNA sequence which unexpectedly drives expression of this series of transcripts has been identified. This sequence provides the advantages as a promoter to drive therapeutic gene expression discussed above.

In this application, we describe the identification of a cluster of genes encoding ORF71–73 which are latently expressed in an A549 cell line stably transduced by HVS-GFP. We have characterised a region of 2000 bp immediately upstream of the coding sequence of ORF73 and demonstrated that this regulatory region, when transfected into a human 293T cell line, is able to drive active expression of the GFP reporter gene. This result demonstrates that the upstream region of ORF73 contains regulatory sequences which may be utilized to drive expression of heterologous transgenes in a range of human cell lines. Therefore we believe that the ORF73 promoter, which drives virus-encoded gene expression whilst the HSV is present in a cell in a latent state, is an ideal choice of regulatory sequence for driving stable long term expression of a transgene in HVS-based gene delivery vectors.

Furthermore, in order to further investigate the possibility of using the ORF73 regulatory region as a promoter to drive long term expression of a heterologous transgene, a number of PCR fragments containing sequence immediately upstream of the ORF73 initiation codon were amplified by PCR and cloned into a reporter plasmid containing the GFP gene. These reporter constructs were transfected into the human 293T cell line and we have demonstrated that some of these fragments contain a regulatory region sufficient to drive heterologous gene expression in a human 293T cell line.

We believe that *Herpesvirus saimiri* (HVS) is an attractive candidate for use as a gene therapy vector as it has the ability to enter a latent mode of infection in which the viral genome is maintained as a stable episome in the host cell.

We have generated a recombinant HVS in which the gene encoding green fluorescent protein (GFP) is expressed under the control of the constitutive human cytomegalovirus (CMV) promoter (HVS-GFP). This recombinant virus is able to stably transduce a range of human cell lines including the lung carcinoma cell line, A549, and direct production of GFP. However, it is known that the human CMV promoter is not effective in many circumstances for sustaining transgene expression in gene therapy in vivo. We have therefore sought to identify promoters which might be functional during latent infection with the HVS vectors.

Statement of the Invention

In the broadest aspect of the invention there is provided a gene delivery system/vaccine comprising a promoter which functions in a vector gene delivery system/vaccine during periods when the gene therapy vector is present in the cell in a latent state. The present invention is capable of regulating long term gene expression in the gene delivery system/vaccine and is capable of controling the expression of transgenes in a range of human or animal cells.

According to a first aspect of the invention there is provided a nucleic acid comprising a nucleic acid sequence which encodes a promoter and which hybridises under high stringency conditions to the nucleic acid sequence of SEQ ID NO:1, fragments and/or variants thereof, for use in gene therapy.

Preferably, hybridisation occurs under stringent conditions such as 1× SSC, 0.1% SDS at 65° C.

Preferably, said promoter comprises a nucleic acid sequence of at least 329 bp and up to 2000 bp, more preferably said promoter comprises a nucleic acid sequence of up to a length of 329, 630, 1000 or 1500 bp or any other selected fragment or variant thereof. It will be appreciated that it is possible that the promoter sequence of the invention may be less than 329 bp so long as the effective sequence encoding the promoter is included in the invention.

According to a second aspect of the invention there is provided a recombinant DNA molecule containing at least one insert comprising the nucleic acid sequence of SEQ ID NO:1, fragment or variant thereof, encoding a promoter.

Thus it will be appreciated that the invention includes nucleic acids comprising (i) a sequence of up to 2000 bp which encodes the promoter, (ii) fragments of selected bp lengths within the sequence and (iii) variants thereof, as well as recombinant DNA molecules containing insert(s) of the promoter sequence therein.

According to a third aspect of the invention there is provided a gene therapy system comprising a vector which includes a nucleic acid sequence selected from the group consisting of the nucleic acid sequence of SEQ ID NO:1, and fragments and variants thereof as well as nucleic acid sequences which hybridise under high stringency conditions to the sequence of SEQ ID NO:1, or a part thereof, wherein said system is capable of driving heterologous gene expression during periods of latent infection by the vector in a target cell population.

Preferably, the gene therapy system further includes any one or more of the features herein before described.

Preferably, said vector additionally comprises at least one therapeutic nucleic acid, whereby the promoter encoded by SEQ ID NO:1 or fragment or variant thereof acts to drive expression of said the at least one therapeutic nucleic acid.

Reference herein to therapeutic nucleic acid is intended to include a therapeutic gene or fragment or variant thereof.

The vector of said gene delivery system may be viral or non-viral.

Preferably, said gene therapy system is capable of long term gene expression.

Reference herein to long term gene expression includes gene expression for at least several hours and optimally at least several months, for example and without limitation, from 2 hours to six months or more.

According to a fourth aspect of the invention there is provided use of a gene therapy system as herein before described for long term gene expression.

It will be appreciated by those skilled in the art that the invention comprises a gene therapy system and that, in preferred embodiments the vector may be either viral or non-viral. The expression of a therapeutic gene can be regulated by a promoter, typically of up at least 329 bp and up to 2000 bp, the system being capable of driving heterologous gene expression during periods of latent infection of a target cell population. Thus, foreign transgenes can be controlled by, for example, a natural promoter, which is active in the latent mode of viral infection. The specifics of the gene expression and the nature of the vector is not intended to limit the scope of the application.

According to a fifth aspect of the invention there is provided an HVS comprising a nucleic acid sequence encoding a promoter of SEQ ID NO:1, or fragment or variant thereof or a nucleic acid sequence which hybridises under high stringency conditions to the sequence of SEQ ID NO:1, fragment or variant thereof, which promoter acts in the latent state, the sequence encoding for the promoter being positioned so as to drive expression of at least one therapeutic nucleic acid which has been inserted in the HVS.

The preferred embodiments of the fifth aspect of the invention include those listed in accordance with the aforementioned first and third aspects of the invention.

Preferably, the HVS of the present invention may be rendered ineffective and its activity terminated by the appropriate co-administration of an anti-herpetic pharmaceutical such as acyclovir.

According to a sixth aspect of the invention there is provided a method of manufacturing an expression vector comprising the promoter of the first aspect of the invention or the gene therapy system of the third aspect of the invention or the HVS vector of the fifth aspect of the invention, the method comprising transfecting a cell with a nucleic acid sequence encoding said promoter of SEQ ID NO:1, or fragment or variant thereof or a nucleic acid sequence which hybridises under high stringency conditions to the sequence of SEQ ID NO:1 or any part thereof.

The invention includes methods which comprise selecting the promoter and amplifying it and subsequently purifying it prior to transfecting a cell population, preferably a selected target cell population.

According to a seventh aspect of the invention there is provided a method of treatment comprising administering a therapeutically effective amount of the promoter of the first aspect of the invention or a gene therapy system of the third aspect of the invention or a HVS gene therapy vector of the fifth aspect of the invention, to an individual requiring treatment.

According to an eighth aspect there is provided the promoter of the first aspect of the invention or the gene therapy system of the third aspect of the invention or the HVS vector of the fifth aspect of the invention for use as a pharmaceutical.

According to a yet further aspect of the invention there is provided a pharmaceutical composition comprising the promoter of the first aspect of the invention or a gene therapy system of the third aspect of the invention or a HVS gene therapy vector of the fifth aspect of the invention, the pharmaceutical additionally comprises a pharmaceutically acceptable excipient, diluent or carrier and ideally said pharmaceutical can be formulated as a nasal spray, or for injection or for oral/paraenteral administration into a individual requiring treatment.

According to a yet further aspect of the invention there is provided use of the promoter of the first aspect of the invention or the gene therapy system of the third aspect of the invention or the HVS vector of the fifth aspect of the invention in the manufacture of a medicament for treating cancer.

According to a yet further aspect of the invention there is provided use of the promoter of the first aspect of the invention or the gene therapy system of the third aspect of the invention or the HVS vector of the fifth aspect of the invention in the manufacture of a medicament for treating degenerative disorders.

According to a yet further aspect of the present invention is an isolated nucleic acid encoding a promoter, the nucleic acid may be selected from the group consisting of:
  (a) DNA having the nucleotide sequence given herein as SEQ ID NO:1 and which encodes the promoter;
  (b) nucleic acids which hybridize to DNA of (a) above (e.g., under stringent conditions) and which encode the promoter; and DNAs of the present invention include those of closely related sequences to, and having essentially the same biological properties as, the promoter disclosed herein, and particularly the DNA disclosed herein as SEQ ID NO:1. This definition is intended to encompass natural allelic variations therein. Thus, DNAs which hybridize to DNA disclosed herein as SEQ ID NO:1 (or fragments or derivatives thereof which serve as hybridization probes as discussed below) and which encode the promoter of the present invention are to be included in the definition.

Conditions which will permit other DNAs which encode the promoter of the present invention and hybridize to the DNA of SEQ ID NO:1 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SDS and 1× SSPE at 42° C., respectively) to DNA of SEQ ID NO:1 disclosed herein in a standard hybridization assay. See, e.g., J. Sambrook et al., *Molecular Cloning, A Laboratory Manual* (2d Ed. 1989) (Cold Spring Harbor Laboratory). In general, sequences which code the promoter of the present invention and which hybridize to the DNA of SEQ ID NO:1 disclosed herein will be at least 75% homologous, 85% homologous, and even 95% homologous or more with SEQ ID NO:1.

The invention will now be described with reference to the following Figures wherein:

FIG. 1 represents SEQ ID NO:1;

FIG. 2 illustrates expression of GFP in A549 cells from episomal HSV-GFP;

FIG. 3 illustrates a schematic representation of the map positions of restriction fragments of the HVS genome;

FIG. 4 illustrates untreated or latency infected A549 cell total RNA separated on 1% denaturing agarose gels, Northern blotted and hybridized with the labelled (a) Eco D fragment and (b) with the labelled Eco J fragment, respectively of HVS genomic DNA;

FIG. 5 illustrates untreated or latency infected A549 cell total RNA separated on 1% denaturing agarose gels, gel electrophoresis, Northern blotted and hybridized with (a) the labelled Eco C fragment and (b) with the labelled KpnE fragment, respectively of HVS genomic DNA;

FIG. 6 illustrates untreated or latency infected A549 cell total RNA separated on 1% denaturing agarose gels, Northern blotted and hybridized with a) ORF71 b) ORF72 c) ORF73;

FIG. 7 illustrates expression of GFP in transfected human 293T cell lines, and Table 1 represents results obtained by Northern blot analysis.

BRIEF DESCRIPTION OF THE FIGURES

FIG. 1. (SEQ ID NO:1) sequence of the 2000 bp promoter.

FIG. 4 Hybridization with the labelled Eco D fragment (a) and the labelled Eco J fragment (b). Each lane was loaded with 6 μg of total RNA and analyzed by Northern blotting and hybridization with the labelled probe. Lane 1 contains extract from uninfected A549 cells; lane 2—A549 cells stably transduced with the recombinant HVS-GFP virus and cultured in the presence of G418 (0.6 mg/ml); lane 3—A549 cells stably transduced with the recombinant HVS-GFP virus and cultured in the absence of G418; lane 4—uninfected OMK cells; lane 5—RNA extracted from OMK cells 8 hours after infection with the recombinant HVS-GFP virus; lane 6—RNA extracted from OMK cells 16 hours after infection with the recombinant HVS-GFP virus; lane 7—RNA extracted from OMK cells 24 hours after infection with the recombinant HVS-GFP virus; lane 8—RNA extracted from OMK cells 48 hours after infection with the recombinant HVS-GFP virus. Hybridization with an Actin probe as a control for amounts of RNA loaded, is shown below.

FIG. 5 Hybridization with the labelled Eco C fragment (a) and Kpn E fragment (b). Each lane was loaded with 6 μg of total RNA and analyzed by Northern blotting and hybridization with the labelled probe. Lane 1 contains extract from uninfected A549 cells; lane 2—A549 cells stably transduced with the recombinant HVS-GFP virus and cultured in the presence of G418 (0.6 mg/ml); lane 3—A549 cells stably transduced with the recombinant HVS-GFP virus and cultured in the absence of G418; lane 4-uninfected OMK cells; lane 5—RNA extracted from OMK cells 8 hours after infection with the recombinant HVS-GFP virus; lane 6—RNA extracted from OMK cells 16 hours after infection with the recombinant HVS-GFP virus; lane 7—RNA extracted from OMK cells 24 hours after infection with the recombinant HVS-GFP virus; lane 8—RNA extracted from OMK cells 48 hours after infection with the recombinant HVS-GFP virus. Again, hybridisation with an Actin probe was used as the control for RNA loading, as shown below.

FIG. 6 Hybridization with a) ORF71 b) ORF72 c) ORF73. Each lane was loaded with 61 g of total RNA and analyzed by Northern blotting and hybridization with the labelled probe. Lane 1 contains extract from uninfected A549 cells; lane 2—A549 cells stably transduced with the recombinant HVS-GFP virus and cultured in the presence of G418 (0.6 mg/ml); lane 3—A549 cells stably transduced with the recombinant HVS-GFP virus and cultured in the absence of G418; lane 4-uninfected OMK cells; lane 5—RNA extracted from OMK cells 8 hours after infection with the recombinant HVS-GFP virus; lane 6—RNA extracted from OMK cells 16 hours after infection with the recombinant HVS-GFP virus; lane 7—RNA extracted from OMK cells 24 hours after infection with the recombinant HVS-GFP virus; lane 8—RNA extracted from OMK cells 48 hours after infection with the recombinant HVS-GFP virus. Actin probe controls are again shown below.

Materials and Methods

Viruses, Cell Cultures and Transfections

Recombinant HVS (Strain A11) was propagated in Owl Monkey Kidney (OMK) cells which were maintained in Dulbecco's modified Eagle medium (Life Technologies) supplemented with 10% foetal calf serum. Human lung carcinoma A549 and 293T cells were maintained in Dulbecco's modified Eagle medium (Life Technologies) supplemented with 10% foetal calf serum. Jurkat cells were maintained in RPMI (Life Technologies) supplemented with 5% foetal calf serum.

For transfection, cells were seeded at approximately $5 \times 10^5$ cells per 35 mm diameter Petri dish 24 h prior to transfection. Plasmids used in the transfections were prepared using the Qiagen Plasmid kits according to the manufacturer's directions. Transfections were performed using Lipofectamine™ (Gibco BRL) as described by the manufacturer using 2 µg of the appropriate plasmid.

Total RNA Extraction

Cells were lysed using Trizol reagent (Life Technologies). Chloroform (0.2 ml) was then added and the solution vortex-mixed for 15 s and stored at room temperature for 5 min. Samples were centrifuged for 15 min at 4° C., and the aqueous phase containing nucleic acids was precipitated using 0.5 ml of isopropanol. The pellet was washed with 70% ethanol, resuspended in 20 µl DEPC-treated water (0.1% solution) and stored at −70° C.

Northern Blot Analysis

Figure 3:
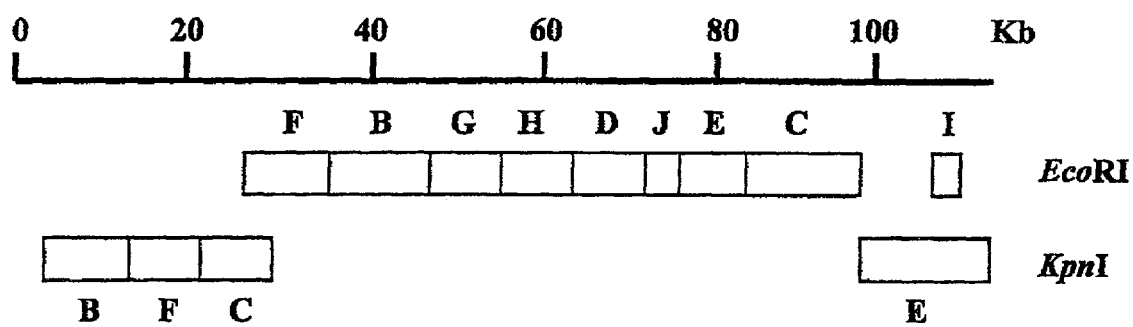

Northern blot analysis was performed essentially as described by Sambrook et al. (1989). Total RNA was isolated from untreated or HVS-transduced A549 cells or from lytically infected OMK cells at 8, 16, 24 and 48 hours post infection, and separated by electrophoresis on 1% denaturing formaldehyde agarose gels. The RNA was transferred to Hybond-N membranes and hybridised with radiolabelled $^{32}$P labelled random primed probes made from restriction fragments derived from the HVS genome (FIG. 3). Hybridisations were performed for 12 hours at 65° C. using ExpressHyb™ buffer (Clontech).

HVS Genomic Probes

The HVS genome can be cleaved with EcoRI and the resultant fragments cloned into the plasmid vector pACYC184 or Kpn I fragments can be cloned into the vectors pJC81 or pWD7 (Knust et al., 1983). These genomic fragments were excised from the vectors by digestion with either EcoRI or Kpn I. The ORF71 gene was amplified by PCR using the primer pair; ORF71F (SEQ ID NO:2) dCGC GGA TCC GGC AAG GTC ACT TCG CCC TAT CTG-3', ORF71R (SEQ ID NO:3) 5'dCCG GAA TTC CTG TGT TAC ACA TAA CAG ACT-3'. The ORF72 gene was amplified using the primer pair; ORF72F (SEQ ID NO:4) 5'dCGC GGA TCC GCT GCA ATG GCA GAT TCA CC-3'; ORF72R (SEQ ID NO:5) 5'dCCG GAA TTC GGT CTG CAG TTA GTG TTG TCA G-3'. The ORF73 gene was amplified using the primer pair ORF73F (SEQ ID NO:6) 5'dACG CGT CGA CCC ATC TAT AAT TGC AAC AAA CAC C-3'; ORF73R (SEQ ID NO:7) 5'd-CCC AAG CTT CAC ATA TAT GAA TGC TAG TGC AC-3'. The PCR (1 cycle of 5 min at 95° C.; 30 cycles of 1 min at 95° C., 1 min at 55° C., 1 min at 72° C.; 1 cycle of 10 min at 72° C.) was performed using 2 U of Klentaq DNA Polymerase (Clontech). Probes were radiolabelled using the Megaprime kit according to the method described by the manufacturer (Amersham).

Plasmids

In order to make the reporter constructs p73.1-4GFP, 632, 1000, 1500 and 2000 bp sequences immediately upstream of the ORF73 initiation codon (FIG. 1) were amplified by PCR (1 cycle for 5 min at 95° C.; 35 cycles 1 min at 95° C., 1 min at 55° C., 1 min at 72° C.; one cycle for 10 min at 72° C.). For p73.1GFP, the primer pair (SEQ ID NO:8) 5'dACG CGT CGA CCC ATC TAT AAT TGC AAC AAA CAC G-3'; (SEQ ID NO:9) 5'dCCC AAG CCT CAC ATA TAT GAA TGC TAG TGC AC-3' were utilised. These primers incorporated terminal HindIII and Sal I restriction sites respectively, for convenient cloning of the PCR product. In order to amplify p73.2-4 the forward primers (SEQ ID NO:10) 5'dGCA CTG CAG CAC CAT CAC ATG AGG AGG TGC-3'; (SEQ ID NO:11) 5'dGCA CTG CAG CCA TGC AGC AGC CAT GCG CTG CC-3' and (SEQ ID NO:12) 5'd-GCA CTG CAG CCC AGA GAG CTG GAC ACT AG-3' and the same reverse primer (SEQ ID NO:13) 5'dCGC GGA TCC CCA TCT ATA ATT GCA ACA AAC ACG-3' were used. These primers contained the restriction sites PstI and BamHI, respectively for convenient cloning of the PCR products. Upon digestion with the appropriate restriction enzymes, the PCR products were cloned into the reporter plasmid pEGFP (Clontech) to derive the expression constructs p73.1-4-GFP, respectively.

Results

Production of stably transduced A549 cell lines with HVS-GFP.

Figure 2:
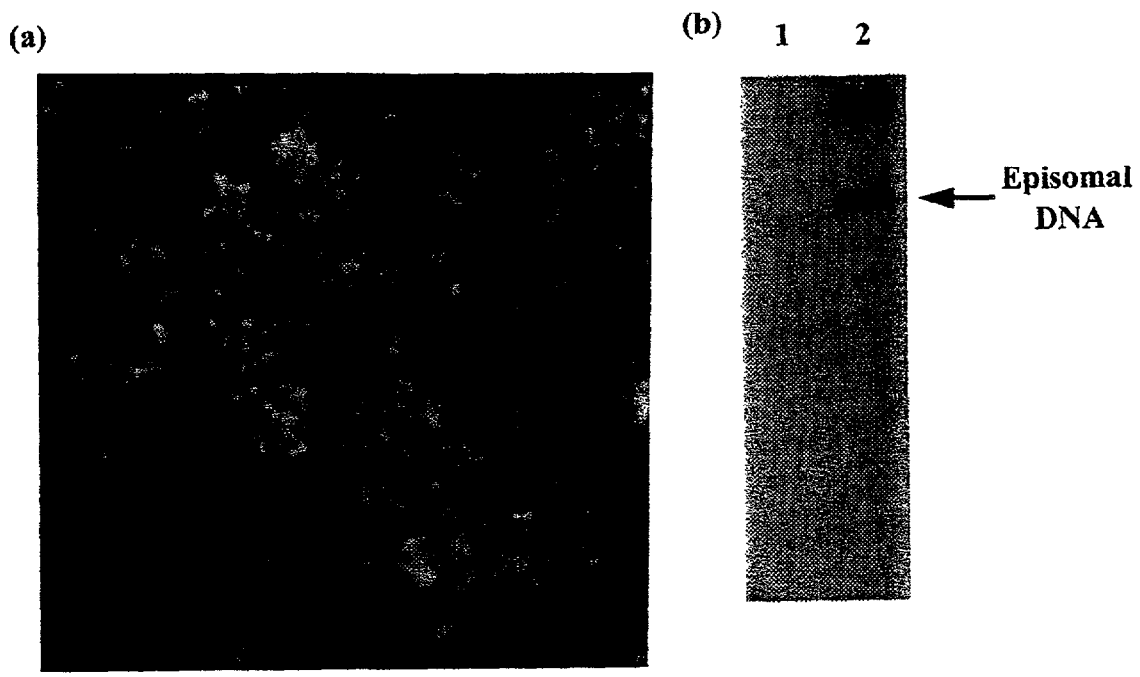
FIG. 2. Expression of GFP in A549 cells stably transduced with a recombinant HVS FIG. 3 A schematic representation of the map positions of restriction fragments resulting from digestion of the HVS genome with either EcoRI or Kpn I. The fragments represent the entire L-DNA region (112 kb) of *H. saimiri*.

In order to identify any HVS latency-associated transcripts which might exist, A549s cells were infected with HVS-GFP and cultured in the presence of G-418. After 48 hours approximately 75% of the cells were found to express the transgene and this increased to 100% by day 12. Fluorescence microscopy confirmed that the GFP protein was expressed in these cells (FIG. 2.a) and Southern blot analysis on viral DNA confirmed that the viral genome was maintained episomally (FIG. 2.b). This cell line formed the basis of the HVS-latency model as the cells remained green, expressing the transgene for 6 months, demonstrating that HVS was stably maintained in a latent episome form (FIG. 2.b).

Transcription Mapping of the HVS Genome in Latently Infected A549 Cells

In order to identify which genes were expressed in the latent episomal state of HVS, Northern blot analysis was performed. Total RNA was extracted from an A549 cell line which had been stably transduced with a recombinant HVS. As controls, total RNA was extracted from a lytic infection of OMK cells at 8, 16, 24 and 48 h.p.i. and from uninfected A549 cells. Northern blots were hybridized with restriction fragments of genomic HVS DNA which spanned the complete coding region of the HVS genome between the two flanking regions of H-DNA. The location of these restriction fragments on the HVS genome is shown in FIG. 3.

Rather than present each Northern blot individually we have chosen to summarize the results of the analysis in Table 1. Only a semi-quantitative estimate of signal intensity has been made, since this depends upon a number of factors including probe length, exposure time, transcript length and the specific activity of the probe. Also, since the aim of this work was simply to identify which genes are transcribed in a latent HVS infection we did not consider it necessary to accurately quantify the intensity of each signal but rather to make a qualitative assessment by comparing signal intensity in A549 cells with that in lytically infected OMK cells.

TABLE 1

|  | Green-A549 | Green Jurkat | Green MIAPACA | Green SW480 |
| --- | --- | --- | --- | --- |
| KpnB | vw | – | – | – |
| KpnC | vw | ND | ND | ND |
| KpnE | + | ND | ND | ND |
| KpnF | vw | – | – | – |
| EcoC | + | – | – | – |
| EcoD | vw | – | – | – |
| EcoE | vw | – | – | – |
| EcoF | vw | – | – | vw |
| EcoG | vw | – | – | – |
| EcoH | vw | – | – | – |
| EcoJ | vw | – | – | – |

(ND = not determined; vw = very weak level of expression)

High levels of gene expression were observed in control lytic OMK cell infections when hybridized with fragments Eco D and Eco J (FIG. 4). The Eco D fragment contains the ORF50 gene, the product of which is a strong transcriptional activator responsible for initiating expression of delayed early (DE) and late viral genes in the lytic cascade. Similarly, the Eco J fragment contains the ORF57 gene, which is activated by ORF50 and also activates expression of DE and late viral genes (Whitehouse et al; 1997b; 1998a; b). In comparison with the levels of gene expression observed in the lytically infected OMK cells, negligible levels of gene expression were detected in the stably transduced A549 cells when probed with Eco D or Eco J. Some low level of lytic gene expression may be due to a very low background of lytic replication occurring in a sub-population of the A549 cells infected with the recombinant HVS. High levels of gene expression were also observed in the lytically infected OMK cells when probed with genomic fragments containing viral DE or late genes but again, negligible gene expression was detected in the stably transduced A549 cells when probed with the same fragments. FIG. 4 shows Northern blots using probes made from the Eco D and Eco J fragments. However, incubation of Northern blots with probes specific for either the Eco C or the Kpn E fragment detected comparable levels of a transcript approximately 6 kb in length in transduced A549 cells as well as lytically infected OMK cells (FIG. 5). Both the Eco C and Kpn E genomic fragments unexpectedly share a region of overlap which contains ORFs 71–73.

ORFs71–73 are Expressed in A549 Cells Stably Transduced with Recombinant HVS

In order to further investigate the pattern of gene expression observed in the stably transduced A549 cells, Northern blot analysis was performed using specific probes for ORF 71–73. The results are shown in FIG. 6. Hybridization with each of the three probes detected two transcripts of approximately 6 kb and 4.4 kb in both stably transduced A549 cells and lytically infected OMK cells. The expression levels of these transcripts in the stably transduced A549 cells are comparable with levels in the lytically infected cells and are very significantly higher than the very low levels of expression detected in these cells when hybridizing with probes containing other genes expressed in the lytic mode of infection, strongly suggesting that unexpectedly these transcripts are expressed in the latent episomal state.

The region immediately upstream of ORF73 contains a promoter which is active in the latent state and which is able to drive expression of a transgene in 293T cells.

The development of HVS as an effective gene delivery vector requires the use of promoters which can drive stable long term expression of heterologous transgenes. Current promoters such as the constitutive HCMV promoter, which have been used to drive expression of GFP in our recombinant HVS, are susceptible to silencing effects which are poorly understood. A viral promoter driving expression of genes active in the latent state would be an ideal candidate for use in regulating long term expression of a foreign transgene. Having identified the active expression of ORF71–73 in cells containing episomally maintained HVS in the latent state, we investigated whether the regulatory region upstream of ORF73 could be utilized to drive expression of a transgene.

Figure 7:
FIG. 7 Expression of GFP in human 293T cell lines. Cells were grown to approximately 70% confluence and transfected with 2 µg of the reporter plasmids p73.1-4-GFP using Lipofectamine according to the protocol described by the manufacturer, Life Technologies.

A number of PCR fragments encompassing 630, 1000, 1500 and 2000 bp of sequence immediately upstream of the initiation codon of ORF 73 were amplified by PCR. The primers used in the PCR were designed so that the final products contained HindIII and Sal I restriction sites at their 5' and 3' termini, respectively. Each PCR product was purified and cloned into the polylinker site of the plasmid, pEGFP to generate the reporter plasmids, p73.1-4GFP, respectively. The reporter plasmids were each transfected into the human 293T cell line and GFP expression analysed by fluorescence microscopy 48 hours post transfection. Results are shown in FIG. 7. All four fragments containing the upstream sequence of ORF 73 are sufficient to drive heterologous gene expression in human 293T cells.

The ability of Herpesvirus saimiri to enter a latent mode of infection in a human cell in which the viral genome is maintained as a stable episome makes this virus an attractive candidate for use as a gene delivery vector. Previously we have described a recombinant HVS containing an expression cassette in which the GFP gene is under the control of the constitutive HCMV promoter. We have shown that this virus is able to stably transduce a range of human cancer cell lines, including the lung carcinoma line, A549. In this cell line the viral genome is maintained as a stable episome and the GFP gene product is produced, demonstrating that HVS can be used as a vector to deliver foreign genes into tumour cells.

Despite some expression of GFP, however, the HCMV promoter is not an ideal choice for driving long term stable expression of a heterologous transgene because it is susceptible to poorly understood silencing effects which reduce the activity of the promoter.

A viral promoter which is active in the latent, non-replicative mode of HVS infection would be the ideal choice for driving stable long term gene expression in an HVS-based gene therapy vector. Identification of genes transcribed in a latent HVS infection would help to identify candidate promoters suitable for use in driving transgene expression in an HVS-based gene delivery vector. We therefore extracted RNA from A549 cells stably transduced with the recombinant HVS-GFP virus and probed with a series of fragments which span the entire coding region of the HVS genome. Hybridization with fragments containing genes encoding immediate early transactivators of the lytic transcriptional cascade detected high levels of gene expression in a lytic infection of OMK cells with the HVS-GFP virus. Similarly, hybridization with fragments containing late genes encoding structural components also detected high levels of gene expression in a lytic infection of OMK cells. In comparison to the lytically infected OMK cells, negligible levels of lytic gene transcription were detected in the stably transduced A549 cells. This may be explained by considering the A549 cells as consisting of two populations of cells, one large sub-population in which the HVS-GFP virus enters a truly latent mode of infection, and a much smaller sub-population of cells in which the HVS-GFP virus may enter a lytic mode of infection. Virus recovery assays from this stably transduced A549 cell line show that a very low level of viral replication does occur.

Hybridization with two specific fragments, Eco C and Kpn E, detected high levels of gene expression in the stably transduced A549 cells comparable with those in infected OMK cells, a permissive cell line. Such a high level of gene expression could not be due to the very low level of lytic replication in A549 cells, since expression of other lytic cycle genes was so low as to be barely detectable in this cell line. A more likely explanation is that the fragments Eco C and Kpn E hybridize to mRNA from genes which are expressed when HVS is in a latent, non-replicative mode of infection as in the majority of the A549 cells.

Analysis of the Eco C and Kpn E fragments revealed that they both contained ORF71–73. Unexpectedly, hybridization of Northern blots with PCR products of ORF71, 72 and 73 detected high levels of two transcripts in both our stably transduced A549 cell line and lytically infected OMK. In each experiment, hybridization with ORF71–73 detected the same transcripts, 6 kb and 4.4 kb in length, suggesting that these genes are transcribed as a polycistronic mRNA from the ORF73 promoter, since this gene lies at the rightmost end of the cluster.

From these studies we conclude that a region including ORF71–73 is expressed in both the lytic and latent modes of HVS infection. Furthermore we believe the regulatory region which expresses the latent transcript is an ideal choice for driving stable long term expression of a transgene. We therefore investigated whether the ORF73 promoter was active in a range of human cell lines to demonstrate whether it could be used to drive a heterologous transgene. A commonly encountered problem with currently used strong promoters such as the HCMV promoter is that their activity is reduced by a silencing effect in a number of cell lines. We speculated that the regulatory region of a latently expressed HVS gene should not be susceptible to this effect and would be an ideal choice for driving expression of foreign genes. Similar problems with silencing have been encountered in Herpes simplex virus (HSV) based vectors. In a latent infection of neurons by HSV, the virus genome is maintained in a nonlinear, episomal, nucleosome bound state and transcription is restricted to a single region encoding two highly abundant, polyadenylated latency associated transcripts (LATs) (Fraser et al., 1992; Stevens et al, 1987). The TATA box and basal transcriptional elements which constitute the LAT promoter reside within an approximately 700 bp region upstream of the 2 kb major LAT (Dobson et al., 1995). This core LAT promoter is not sufficient to drive prolonged reporter gene expression during latency however, as regulatory elements found within the first transcribed 1.5 kb LAT sequences have also been found to be necessary for full promoter activity (Lokensgard et al., 1994; Perng et al, 1996). The majority of heterologous promoters used in HSV-based vectors have all resulted in either transient or low-level, long-term gene expression in only a small proportion of transduced cells (Bloom et al., 1995; Ecob-Prince et al., 1995; Lachmann et al., 1996). Recently, however, the upstream and downstream elements of the LAT promoter have been used to drive expression of lacZ and lacZ-neo reporter genes in a recombinant HSV-1. After peripheral infection this recombinant HSV was capable of driving stable, long-term expression of β-galactosidase in the peripheral nervous system of mice for at least 190 days postinfection (Lachmann et al., 1997).

In order to determine whether regulatory sequences governing the expression of ORF73 could be used similarly to drive foreign gene expression we constructed reporter plasmids, p73.1-4GFP, in which the GFP gene was placed under the control of the various PCR fragments encoding sequences immediately upstream of the ORF 73 gene. Transfection of the reporter constructs into 293T cells showed that GFP was expressed at high levels, indicating that the minimal functional ORF73 promoter was contained within the 632 bp upstream of ORF73 and that this promoter could drive expression of a heterologous transgene in a human cell line.

In conclusion, we have found three genes, ORF71, 72, and 73 which are expressed by HVS when maintained as a stable, non-replicating episome in human A549 lung cancer cells. We have also shown that the upstream regulatory sequences of the ORF73 coding region are sufficient to drive expression of a foreign transgene in a human 293T cell line. We believe that this is of crucial importance to the development of HVS as an effective gene therapy vector since foreign transgenes can now be placed under the control of a natural HVS promoter which is active in the latent mode of viral infection.

REFERENCES

Albrecht J-C. Nicholas J, Biller D, Cameron K R, Biesinger B, Newman C, Wittmann S, Craxton M A. Coleman H, Fleckenstein B, Honess R W. Primary structure of the *Herpesvirus saimiri* genome. *J Virol* 1992; 66: 5047–5058.

Bankier A T, Dietrich W, Baer R, Barrell B G, Colbere-Garapin F, Fleckenstein B, Bodemer W. Terminal repetitive sequences in *herpesvirus saimiri* virion DNA. *J Virol* 1985; 55: 133–139.

Bloom D C, Maidment N T, Tan A, Dissette V B, Feldman L T, Stevens J G. Long-term expression of a reporter gene from latent herpes simplex virus in the rat hippocampus. *Brain Res Mol Brain Res* 1995; 31: 48–60.

Blubot M, Manet E, Lequarre A S, Albrecht J-C, Nicholas J, Fleckstein B, Pastoret P P, Thiry E. Genetic relationships between bovine herpesvirus 4 and gamma-herpesvirus Epstein-Barr and *herpesvirus saimiri*. *Virology* 1992; 190: 654–665.

Dobson A T, Margolis T P, Gomes W A, Feldman L T. In vivo deletion analyses of the herpes simplex virus type 1 latency-associated transcript promoter. *J Virol* 1995; 69: 2264–2270.

Ecob-Prince M S, Hassan K, Denheen M T, Preston C M. Expression of beta-galactosidase in neurons of dorsal root ganglia which are latently infected with herpes simplex virus type 1. *J Gen Virol* 1995; 76: 1527–1532.

Fink D J, DeLuca N, Goins W, Glorioso J. Gene transfer to neurons using herpes simplex virus-based vectors. *Ann Rev Neurosci* 1996; 19: 265–287.

Fleckenstein B, Desrosiers R C. *Herpesvirus saimiri* and herpesvirus ateles, p253–332. In B. Roizman (ed.), The herpesviruses, vol. 1. Plenum Press. New York, 1982.

Fraser N W, Block T M, Spivack, J G. The latency-associated transcripts of herpes simplex virus: RNA in search of a function. *Virology* 1992; 191: 1–8.

Glorioso J C, DeLuca N A, Fink D J. Development and application of herpes simplex virus vectors for human gene therapy. *Ann Rev Micro* 1995; 49: 675–710.

Glorioso J C, Goins W F, Fink D J. Herpes simplex virus based vectors. *Seminars in Virology* 1992; 3:265–276.

Knust E, Schirm S, Dietrich W, Bodemer W, Kolb E, Fleckenstein B. Cloning of *Herpesvirus saimiri* DNA fragments representing the entire L-region of the genome. *Gene* 1983; 25: 281–289.

Lachmann R H, Brown C, Efstathiou, S. A murine RNA polymerase I promoter inserted into the herpes simplex virus type 1 genome is functional during lytic, but not latent, infection. *J Gen Virol* 1996; 77: 2575–2582.

Lachmann R H, Efstathiou S. Utilization of the Herpes Simplex Virus Type 1 latency-associated regulatory region to drive stable reporter gene expression in the nervous system. *J Virol* 1997; 71: 3197–3207.

Lokensgard J R, Bloom, D C, Dobson A T, Feldman L T. Long-term promoter activity during herpes simplex virus latency. *J Virol* 1994; 68: 7148–7158.

Medveczky P, Szomolanyi E, Desrosiers R C, Mulder C. Classification of herpesvirus saimiri into 3 groups based on extreme variations in a DNA region required for oncogenicity. *J Virol* 1984; 52: 938–944.

Perng G-C, Ghiasi H, Slanina S M, Nesburn A B, Wechsler, S L. The spontaneous reactivation function of the herpes simplex virus type 1 LAT gene resides completely within the first 1.5 kb of the 8.3 kb primary transcript. *J Virol* 1996; 70: 976–984.

Sambrook J, Fritsch E F, Maniatis T. Molecular cloning: a laboratory animal, $2^{nd}$ ed. Cold Spring Harbour Laboratory Press, Cold Spring Harbour, N.Y. 1989.

Stevens J G, Wagner E K, Devi, R G, Cook, M L, Feldman, L T. RNA complementary to a herpesvirus alpha gene mRNA is prominent in latently infected neurons. *Science* 1987; 235: 1056–1059.

Virgin, H W, Latreille, P, Wamsley, P, Hallsworth, K, Weck, K E, Dal Canto, AJ, and Speck, S H. Complete sequence and genomic analysis of murine gammaherpesvirus 68. *J. Virol.* 1997; 71: 5894–5904.

Whitehouse A, et al. The *herpesvirus saimiri* ORF50 gene encoding a major transcriptional activator homologous to the EBV R protein, is transcribed from two distinct promoters of different temporal phases. *J Virol* 1997a; 71: 2550–2554.

Whitehouse A, et al. Identification of a cis-acting element within the *herpesvirus saimiri* ORF6 promoter that is responsive to the HVS.R transactivator. *J Gen Virol* 1997b; 71: 1411–1415.

Whitehouse A, Cooper M, Hall K T, Meredith, D M. The open reading frame (ORF) 50a gene product regulates ORF57 gene expression in *Herpesvirus saimiri*. *J Virol* 1998a: 72: 1967–1973.

Whitehouse A. and Stevenson. Gene regulation in *Herpesvirus saimiri* and its implication towards the development of a novel gene therapy vector. *Gene Therapy and Molecular Biology*, 1998b; 3: 35–44.

The invention claimed is:

1. An isolated nucleic acid encoding a latency promoter, wherein the latency promoter is operatively linked to a heterologous gene and drives expression of said heterologous gene in human cells, and wherein the latency promoter comprises at least 630 bp of nucleotides 1362–2000 of SEQ ID NO:1 and up to 2000 bp of nucleotides 2–2000 of SEQ ID NO:1.

2. A nucleic acid according to claim 1, wherein said latency promoter is encoded by a nucleic acid sequence of a length no greater than a length selected from the group consisting of 630 bp, 1000 bp and 1500 bp of SEQ ID NO:1.

3. A recombinant DNA molecule comprising at least one insert that encodes a latency promoter operatively linked to a heterologous gene and drives expression of said heterologous gene in human cells, wherein the latency promoter comprises at least 630 bp and up to 2000 bp of the nucleic acid sequence immediately upstream of the initiation codon of ORF73 of HVS, as set forth in SEQ ID NO:1.

4. The recombinant DNA molecule according to claim 3, wherein said latency promoter comprises a nucleic acid sequence of up to a length no greater than 630 bp of SEQ ID NO:1.

5. An isolated nucleic acid encoding a latency promoter, wherein said latency promoter is operatively linked to a heterologous gene and drives expression of said heterologous gene in human cells, and wherein said isolated nucleic acid comprises nucleotides 2–2000 of SEQ ID NO:1.

* * * * *

UNITED STATES PATENT AND TRADEMARK OFFICE
CERTIFICATE OF CORRECTION

PATENT NO.        : 7,227,012 B1
APPLICATION NO. : 09/913970
DATED             : June 5, 2007
INVENTOR(S)      : Markham et al.

Page 1 of 1

It is certified that error appears in the above-identified patent and that said Letters Patent is hereby corrected as shown below:

Column 7, Line 2:  Please correct "loaded with 61 g of"
                              To read -- loaded with 6µg of--

Signed and Sealed this

Second Day of October, 2007

JON W. DUDAS
*Director of the United States Patent and Trademark Office*